United States Patent [19]

Kraemer et al.

[11] Patent Number: 4,839,419
[45] Date of Patent: Jun. 13, 1989

[54] METHOD FOR IMMOBILIZING DISSOLVED PROTEINS

[75] Inventors: Dieter Kraemer, Mainz; Hermann Plainer, Reinheim; Bruno Sproessier; Helmut Uhlig, both of Rossdorf; Reiner Schnee, Darmstadt, all of Fed. Rep. of Germany

[73] Assignee: Rohm GmbH, Darmstadt, Fed. Rep. of Germany

[21] Appl. No.: 161,204

[22] Filed: Feb. 16, 1988

Related U.S. Application Data

[63] Continuation of Ser. No. 853,736, Apr. 18, 1986, abandoned.

[30] Foreign Application Priority Data

Apr. 27, 1985 [DE] Fed. Rep. of Germany ....... 3515252

[51] Int. Cl.$^4$ .............. C07K 17/00; C12N 9/84; C12N 11/00; C12Q 1/00
[52] U.S. Cl. ............................ 525/54.1; 530/412; 530/413; 210/656
[58] Field of Search ............... 525/54.1; 530/412, 413; 210/656

[56] References Cited

U.S. PATENT DOCUMENTS

| 3,767,531 | 10/1973 | Olsen et al. | 435/180 |
| 3,983,000 | 9/1976 | Messing et al. | 435/176 |
| 4,323,650 | 4/1982 | Rosevear | 435/174 |
| 4,371,612 | 2/1983 | Matsumoto et al. | 435/44 |
| 4,390,626 | 6/1983 | Chibata et al. | 435/176 |
| 4,425,434 | 1/1984 | Rosevear | 435/176 |
| 4,440,903 | 3/1984 | Goldstein et al. | 525/54.1 |
| 4,486,549 | 12/1984 | Matsomoto et al. | 521/53 |

FOREIGN PATENT DOCUMENTS

| 26672 | 4/1981 | European Pat. Off. |
| 37667 | 10/1981 | European Pat. Off. |
| 3336257 | 4/1984 | Fed. Rep. of Germany |
| 1557944 | 12/1979 | United Kingdom |
| 1568328 | 5/1980 | United Kingdom |
| 2128620 | 5/1984 | United Kingdom |
| 2129809 | 5/1984 | United Kingdom |

*Primary Examiner*—John Kight
*Assistant Examiner*—Nathan M. Nutter
*Attorney, Agent, or Firm*—Curtis, Morris & Safford

[57] ABSTRACT

Methods for adsorbing a protein, for example an enzyme, onto an insoluble, solid, macroporous, small-particle support by washing said support with an aqueous solution of the protein containing an electrolyte in an ionic strength of at least 0.15 mole/liter and crosslinking said protein, before, during, or after such adsorption, with a coupling component present in aqueous electrolyte-containing solution.

7 Claims, No Drawings

METHOD FOR IMMOBILIZING DISSOLVED PROTEINS

This application is a continuation application of Ser. No. 853,736 filed Apr. 18, 1986 and now abandoned.

The present invention relates to a method for immobilizing proteins, particularly enzymes, when dissolved in water, on a solid substrate in the presence of an electrolyte.

Immobilized enzymes have already been obtained by crosslinking dissolved enzymes with glutaraldehyde. It has been observed that increasing ionic strength promotes this crosslinking, which has been attributed to the precipitating action of electrolytes. (See K. Ogata et al., Biochim. Biophys. Acta, 159 [1968], 405–407).

Glutaraldehyde has also been used to bind dissolved enzymes to an insoluble support. (See A. Habeeb, Archives of Biochemistry and Biophysics, 119 [1967], 264–268). In contrast with the precipitation and crosslinking of proteins with glutaraldehyde without a support, binding of a protein to solid supports has always been carried out at low electrolyte concentrations.

In the process described in published German patent application DOS 33 36 257, permanently immobilized enzymes are produced by impregnating a porous support, for example diatomaceous earth, with an enzyme solution or by coating a support with a layer of the solid enzyme, and then introducing these preparations comprising a support and a dissolved or solid enzyme into an aqueous saline solution and allowing a crosslinking agent to act on them. The saline solution has the effect that no enzyme is stripped from the enzyme preparation and lost for immobilization. This process thus requires basically two separate process steps: production of an enzyme preparation comprising a support and a dissolved or soluble enzyme, and introduction of the enzyme preparation into a crosslinking bath.

The binding of a fungal lactase with glutaraldehyde to a support formed by macroporous ion exchange resins is described in European Pat. No. 37667, while European Pat. No. 26672 describes such binding to supports consisting of macroporous amphoteric ion exchange resins. In both processes, electrolytes are used a buffer substances only before or after the reaction with glutaraldehyde, whereas during the reaction itself they are used only in low concentrations which in no case exceed 0.05 mole/liter, in order that the ionic adsorption not be vitiated. Indeed, to the contrary, high ion concentrations are mentioned as a means for stripping from the support such amounts of enzyme as may have remained uncrosslinked. Amphoteric or cationic carrier resins may give rise to a variety of troublesome interactions with dissolved constituents of the substrate liquids and therefore are often unsuitable for use.

The present invention accomplishes the object of immobilizing dissolved proteins on macroporous supports with high recovery of the initial activity (high activity yield) in a simple manner in a one-step process.

It has been found that the immobilization of dissolved proteins on a solid macroporous support which is water insoluble, or at most slightly swellable in water, can be carried out in a one step process if an aqueous protein solution containing an electrolyte and having an ionic strength of at least 0.15 mole/liter is allowed to wash over the support until the protein has been adsorbed thereon. If purely adsorptive immobilization is sufficient, the loaded support can simply be separated. As a rule, however, immobilization is stabilized by means of a crosslinking agent. In accordance with the invention, such crosslinking is carried out directly in the electrolyte-containing solution without prior separation of the protein-loaded support. Both during the adsorption and in the binding by means of a crosslinking agent which usually follows, a supernatant of the electrolyte-containing solution is present so that the particles of the support which are suspended or form a column packing are completely washed over.

It is surprising that immobilization of the protein on the macroporous support according to the present invention is promoted by high ionic strengths over the range here disclosed, since high ionic strengths are generally regarded as a means for stripping protein molecules that are not covalently crosslinked from a support and for forming insoluble precipitates without a support in the presence of crosslinking agents.

Following Table I shows the increase in recovery of activity in the binding of penicillinamidase to phenylsepharose with glutaraldehyde as a function of increasing ionic strength. The binding method corresponded to the procedure used in Example 5.

TABLE I

| Potassium phosphate buffer | | Activity of support-bound enzyme | |
|---|---|---|---|
| Molarity (mole/liter) | Ionic strength (mole/liter) | IU per gram moist weight | Percent Yield of immobilized activity |
| 0.01 | 0.03 | 64 | 36 |
| 0.05 | 0.15 | 103 | 51 |
| 0.10 | 0.30 | 128 | 72 |
| 0.50 | 1.50 | 170 | 92 |

Without the use of glutaraldehyde, no immobilized activity is observed under otherwise identical conditions.

The advantages of the procedure preferred in accordance with the invention over immobilization on an amphoteric support is illustrated by the example of the immobilization of yeast lactase. According to comparative Example 1 of European Pat. No. 26672, yeast lactase was immobilized on an amphoteric phenol-formaldehyde ion exchange resin at pH 6.65 and 20° C.–22° C. with glutaraldehyde in a quantitative yield of 64 percent. However, the activity was so low that practically no recovery of activity was obtained.

However, if yeast lactase is bound at 23° C. to beads of a macroporous neutral carrier resin comprising crosslinked acrylamide having oxirane groups as the active coupling groups from an aqueous solution containing 111 g/l of the enzyme preparation, the following activity yields are obtained as a function of the electrolyte concentration used:

TABLE II

| Electrolyte concentration (mole $K_2HPO_4$,$KH_2PO_4$/liter) | Ionic strength (mole/liter) | Activity yield (percent of initial activity) |
|---|---|---|
| 0.5 | 1.21 | 3.5 |
| 1.0 | 2.42 | 19 |
| 1.25 | 3.02 | 51 |
| 1.5 | 3.33 | 55 |

What is particularly surprising is that the method of the invention makes it possible readily to obtain high absolute activities and outstanding activity yield even on widely differing nonspecific supports, which absolute activities and yields otherwise could be obtained only after a complicated activation of the support. Once crosslinked, the protein remains bound to the support even at low ionic strength and, in the case of enzymes for example, can be reused many times without appreciable losses of activity.

The process of the invention is particularly suited for the production of all kinds of solid macroporous bodies which contain soluble proteins in immobilized form. The principal use of the invention is the production of carrier bound enzymes. Other important uses are the production of column packings for affinity chromatography and the production of diagnostic test bodies.

The proteins which can be immobilized according to the invention are those proteins which are sufficiently water soluble at temperatures between 0° C. and 60° C. to be brought into contact in dissolved form with a support. The invention is not limited to particular proteins of this kind but is applicable to any biogenic, water soluble material containing protein. Although a complete failure of the process of the invention has not been observed so far, the possibility cannot be ruled out that it may not be feasible to bind a particular protein to supports, or then only with poorer results than by other methods. It can be advantageous to stabilize the protein by adding ions or, in the case of enzymes, by using substrate additives. Thus, it is known in the art that many proteins are more stable to inactivation when in the presence of certain ions, for example calcium or magnesium ions. Salts of these ions can be added to protein solutions to stabilize them. Similarly, many enzymes are more stable to inactivation in the presence of the substrate toward which they are active. For example, amyloglucosidase is stabilized by dextrin.

Enzymes are preferred and, of these, hydrolases, especially those which cleave low molecular weight (less than about 2000) substrates, particularly sugars such as lactose. Preferred hydrolases are the lactases, invertases, acrylases, and penicillin amidase. Other enzymes include amylases, proteases, amidases, pectinases, cellulases, hemicellulases, isomerases, and oxidases. Illustrative of nonenzymatic proteins are antibodies, hormones having a protein structure, and enzyme inhibitors.

The support may be any solid, whether natural or synthetic, organic or inorganic, having a macroporous structure and which is insoluble in water or aqueous electrolyte solutions. Suitable solids with a macroporous structure have pores of a diameter of at least 10 nanometers (nm) and a pore volume of over $0.1$ cm$^3$/g, and preferably over $0.5$ cm$^3$/g. Preferred supports have pore diameters ranging from 10 to 100 nm, a specific surface from 10 to 500 m$^2$/g, and a pore volume from 1 to 3 cm$^3$/g.

The outer shape of the support is not critical for its effect, although high surface area systems having a specific surface of at least 1 m$^2$/g are often preferred because they permit a large amount of activity of the immobilized protein to be bound in a small space. Suitable supports include the internal surfaces or coatings of vessels or pipes or of built-in structures in vessels or pipelines, and foils, membranes, papers, woven fabrics, nonwoven fabrics, fibrous or other packings, or beddings of solid bodies around or through which flow is possible. When there are sufficiently large spaces between these bodies through which flow is possible, the supports, or at least their layers close to the surface, are able to swell considerably without impeding flow through them. The supports are preferably of small size, meaning supports having a particle size of less than 10 mm and preferably ranging from 0.1 to 5 mm. Particularly preferred are beads, that is, spherical supports. Advantageously, these small size supports do not swell, or do not swell significantly, in the aqueous medium in which they are used, preferably to not more than twice the bulk volume of the dry material. A requirement for the suitability of small size supports is that they lend themselves to being suspended in the electrolyte containing solution by stirring, or permit flow through them when used as column packing.

Most preferred are solid supports which are not cationically charged. This is intended to mean solids which contain no covalently bound cationic groups or basic groups which can be converted by protonation into cationic groups, in other words ammonium or amino groups, or in any case contain not more than 0.1 milliequivalent/gram of such groups in their matrix or at least on their accessible surface. Particularly preferred are macroporous solids which are uncharged or, if charged, carry only a weak anionic charge. Uncharged solids here means solids which do not contain any, or contain not more than 0.1 milliequivalent, of covalently bound carbonyl, carboxylate, sulfonate, amino, or ammonium groups per gram of dry carrier resin. Weakly anionic carrier resins may contain anionic groups, such as covalently bound carboxyl or carboxylate groups, in a concentration up to 5 milliequivalents per gram. These values apply in any case to the resinous material on the active surface of the particles of the support.

However, it has been found that superficial salting out of the protein under the influence of the increased salt concentration can occur also on very hydrophilic surfaces, and even on solids carrying strong anionic charges. Such supports therefore are also suitable for use.

Binding of the proteins is strongly promoted by hydrophobic groups, for example by saturated or, preferably, unsaturated aliphatic hydrocarbon side groups having two or more carbon atoms, or by aromatic hydrocarbon groups. The size of these groups is less important than their density on the surface of the support. Preferred supports consist, at the surface of the pore wall or throughout, of a polymeric material containing at least one weight percent of side groups of the type mentioned.

In principle, macroporous inorganic supports such as glass beads or glass fibers (for example, controlled pore glass), silicic acid, alumina, or activated charcoal are also suitable for use. Organic materials, and particularly synthetic resins, offer the advantage that supports having a specific form, for example, beads, fibers, foils, and coatings, can be more readily produced therefrom. The chemical makeup of the organic support is not critical, although care should be taken in each case to determine which support will produce the best results.

Suitable water insoluble macroporous synthetic resins may be of a nonpolar nature, for example, and may be uncrosslinked or crosslinked, such as polymethyl methacrylate and other acrylate polymers, polystyrene, cellulose esters, phenol-formaldehyde resins, epoxy resins, or polyolefins. They may also be polar and more or less hydrophilic but water insoluble due to crosslinking. Examples are crosslinked cellulose derivatives and starch derivatives, crosslinked polyacrylamide or polymethacrylamide, crosslinked polyhydroxyalkyl esters of acrylic or methacrylic acid, crosslinked polyvinylpyrrolidone, or nonbasic aminoplast resins.

For improvement of the adsorptive properties it is often advantageous to hydrophobize the support somewhat, at least superficially. For example, phenyl groups may be superficially incorporated onto inorganic supports such as silica, bentonite, or porous glasses by reaction with phenyl-functional silanes. Macroporous organic supports such as Sepharose can be analogously phenylated with phenyl glycidyl ether or alkylated with alkyl glycidyl ether. In addition to phenyl groups, all linear or branched alkyl groups having from 1 to 18 carbon atoms generally have an adsorption promoting action.

A particularly well suited group of carrier resins in the form of beads or hollow beads is obtainable in the manner described in U.S. Pat. Nos. 4,070,348, 4,190,713, and 4,208,309, incorporated herein by reference. These are crosslinked polymers with a hydrophilic matrix which have no, or only low, swelling capacity and which are preferably composed in large measure of acrylamide, methacrylamide, and methylenebis-acrylamide or -methacrylamide having crosslinking action. They contain groups possessing binding activity for proteins, and especially epoxy groups since the latter will not form ionic groups by hydrolysis or during the reaction with the protein. Moreover, they contain about 2 to 5 weight percent of free methacryloyl or isopropanyl groups stemming from crosslinker molecules that have been reacted only unilaterally. When such supports are employed, the use of a separate crosslinking agent can be dispensed with.

In the method of the invention, the electrolyte, it is speculated, has the effect of bringing about a kind of supersaturation of the protein, or at any rate a diminution of its solubility, because of structural ordering of water molecules. It is often advantageous to add the electrolyte only after the protein has dissolved as otherwise the latter will occasionally dissolve only haltingly, if at all.

Which electrolyte has a precipitating effect in what concentration depends on the nature of the protein, its concentration, and its impurities, and will have to be determined in each case by trial. In general, all electrolytes which have a salting out effect are usable, for example all salting out anions of the Hofmeister series, including chloride. Examples for the varying effectiveness of electrolytes are given by H. M. Rauen in "Biochemisches Taschenbuch", part 2, 2nd ed., pp. 56–57. Electrolytes which have a positive value of $K_s$ in accordance with the equation $$\log \frac{S}{S_o} = -K_s \times I$$

or with log
$S_o = \beta$
$\log S = \beta - K_s \times I,$ where I is ionic strength, S is the solubility of the protein in the presence of the electrolyte, $S_o$ the solubility of the protein in the absence of the electrolyte, are suitable. Polyvalent metal cations frequently having a precipitating or inactivating effect, so that univalent cations, and particularly alkali ions and ammonium ion, are therefore to be preferred. Anions have a more pronounced influence on the effect of the electrolyte addition. Sulfates, phosphates, and polyphosphates are best suited. Carbonates, chromates, acetates, citrates and tartrates also exert a strong salting out effect but cannot always be used with sensitive proteins. Univalent anions such as chlorides or acetates must be used in higher concentration than polyvalent anions to reach the necessary ionic strength. To be able to exert their salting out effect, polyvalent anions must be used in high concentration. Because of their high effectiveness, low cost, and innocuousness for most proteins, structure forming neutral salts such as ammonium sulfate, sodium sulfate, and potassium sulfate and ammonium, sodium, or potassium bisulfates are best suited. The pH value of the protein solution containing electrolyte depends o the sensitivity of the protein and is preferably in the range from 4 to 9. $K_s$ values, as defined above, follow the Hofmeister series, proceeding from larger to smaller values: citrate, tartrate, sulfate, acetate, chloride, nitrate, bromide, iodide, and thiocyanate, among the anions and thorium, aluminum, barium, strontium, calcium, potassium, sodium, and lithium, among the cations. (cf. Rauen, loc. cit.)

The effectiveness of the electrolyte addition is determined by its ionic strength I. For an aqueous solution containing i ionic species, ionic strength is calculated by the formula $$I = \frac{1}{2} \sum_{i=1}^{i} Z_i^2 C_i,$$

where $C_i$ is the molar concentration and $Z_i$ is the valence of an ionic species. For example, for a 1 M $K_2HPO_4$ solution wherein $C_K=2$, $C_{HPO4}=1$, $Z_K=1$, and $Z_{HPO4}=2$, the ionic strength, I, is 3. In practice, the concentrations of the preferred electrolytes are in the ionic strength range from 0.15 to 2 moles/liter. The ionic strength is preferably at least 0.3 mole/liter.

Immobilization generally begins with an adsorption step. Even when a crosslinking agent is used, the crosslinking reaction is preceded by the adsorption step. The two steps may be carried out successively in that sequence, that is first the protein is adsorbed onto the support in the presence of the electrolyte and then the crosslinking coupling component is added. This is the preferred sequence. However, the two steps can also be combined in the process and the coupling component can already be allowed to react along with the electrolyte during the adsorption. Finally, in many cases it is also possible to first react the support with the coupling component alone and then to add the protein and the electrolyte.

Adsorption of the protein occurs in the system formed by a supernatant of the aqueous protein solution and by the support material over a period from 0.1 to 100 hours, and preferably from 1 to 10 hours. It is important that the electrolyte wash all over the particles of the support in both reaction stages. Immobilization is accelerated as the temperature rises. The operating temperature is preferably the highest temperature with the protein can withstand without loss of activity. Although immobilization can be carried out even at 0° C., temperatures above 40° C., and in many cases above 50° C., are particularly advantageous.

The proteins to be immobilized can be used in a wide range of concentrations, for example from 0.01 to 30 percent, by weight of the solution, and in a wide range of ratios of their amount with respect to the amount of support material. In the case of enzymes, a high binding yield and a high product activity are sought. The loading generally is greater than 20 mg of protein per gram of dry support material, that is, 2 weight percent or more. On the other hand, low loading densities are more advantageous for immobilized ligands used for the isolation of biomacromolecules.

Immobilization may be carried out by suspending the support in the protein solution and then stirring moderately from the time after the electrolyte is added until the process is completed. The protein solution containing electrolyte may also be caused to flow through a packing, formed by the support material, in a column reactor and recirculating the solution for an extended period of time.

Immobilization initially involves only the adsorption of the protein onto the support. When the loaded support is then transferred to an environment poorer in electrolyte, desorption is likely to occur in many cases. This is prevented by the subsequent covalent binding of the protein molecules to one another or to the support. For this purpose, a coupling or crosslinking component is added during the second reaction stage. As mentioned earlier, this can be done even during the adsorption step.

The coupling component must be soluble in the aqueous electrolyte solution in an amount that is at least sufficient for immobilization of the protein. It is important that this component be used in a supernatant of the electrolyte solution, in other words the solution must not be completely absorbed by the support material. Not less than about 0.2 ml, and preferably up to 10 ml, of electrolyte solution should be used per milliliter of moist support material. Moreover, the coupling component must react in the presence of the electrolyte in order that the precipitating action of the latter may be sustained until the protein has been irreversibly immobilized.

Suitable coupling components are compounds having at least limited water solubility and two or more functional groups with which they are able to react with corresponding functional groups of the protein, and optionally also with functional group of the support. Irreversible immobilization may be brought about by a crosslinking of the protein within itself or by crosslinking it with the support. Suitable functional groups which are reactive toward proteins are aldehyde, epoxy, diazo, isocyanate, and chloroformate groups, for example. Carboxyl anhydride or ester groups are in many cases less advantageous because they strongly alter the electrochemical nature of the support by the formation of anionic carboxylate groups. Illustrative of suitable coupling components are diazobenzidine, hexamethylene diisocyanate, chloroformic acid ethyl ester, and glutaraldehyde, the most important compound. Water soluble low molecular weight polymers having molecular weights below 100,000, for example polyacrolein and copolymers of acrylamide or methacrylamide with glycidyl acrylate or methacrylate or with acrolein or with N-allylmethacrylamide may also be used.

Mention should also be made of coupling components which are activated only by the action of ultraviolet radiation or by agents forming free radicals (redox initiators), for example diallyl ethers or copolymers of acrylamide or methacrylamide with para-toluylhydroxyethyl methacrylate.

The amount of coupling component required for irreversible immobilization depends on its reactivity with respect to the protein, and possibly with respect to the support, and may range from 1 to 100 percent of weight of the protein. The reaction conditions for coupling generally do not differ from those of the adsorption so that both processes can take place under the same conditions. In coupling with glutaraldehyde, a reaction time from 0.1 to 100 hours, and preferably of about 2 hours, at temperatures ranging from 0° C. to 80° C. is usually sufficient.

After the immobilization reaction, the electrolyte solution, which may contain unbound residues of the protein and of the coupling component, is usually separated from the loaded support. The latter is then washed with an appropriate buffer solution and is then available for commercial use. Activity values not found in the residual electrolyte solution or found to the support are lost (i.e. inactivated during the process).

A better understanding of the invention and of its many advantages will be had by referring to the following Examples, given by way of illustration.

EXAMPLE 1

Immobilized glucose isomerase

Support: Macroporous highly crosslinked styrene/-divinylbenzene beads having an inner surface area of about 200 m$^2$/g and an average pore diameter of 40 nm.

Enzyme: Glucose isomerase, liquid concentrate from a culture of *Streptomyces albus*.

Activity: 1 g of enzyme converts D-glucose from a 0.1 molar solution at pH 7 and 70° C. to 5 g of D-fructose in 60 minutes.

Coupling: First the enzyme is adsorbed onto the macroporous support. To this end, 10 g of support and 10 g of enzyme in 50 ml of saline solution containing 12% of sodium sulfate, 5% of magnesium sulfate, and 0.02% of cobalt sulfate are rolled at room temperature (23° C.) on a roller table. The ionic strength of the aqueous solution is 4.18 moles/liter. The pH value was adjusted to 7.0. After 20 hours, 0.5 g of glutaraldehyde is added and rolling is continued. The adsorbed enzyme is crosslinked and retained in the pores by this process.

Filtration by suction and washing follow 2 hours later. A comparative activity determination shows an activity of 45% in the filtrate and of 37% in the support.

Activity Yield: 37%.

Use: The immobilized glucose isomerase is used as packing in a column reactor. At a temperature of 60° C. and a throughput rate of seven times the fixed-bed volume per hour, a 40% glucose solution of pH 7.5 is isomerized to fructose with 45% conversion.

EXAMPLE 2

Immobilized Aspergillus oryzae lactase

Support: Crosslinked polyacrylic ester; average pore diameter, 25 nm; inner surface area, 140 m$^2$/g; beads from 0.3 to 1 mm in diameter.

Enzyme: *Aspergillus oryzae* lactase, powdered concentrate. Activity: 30,000 U/g.

Coupling: 10 g of support are shaken with 1 g of enzyme preparation in 40 ml of saline solution at 35° C. for 8 hours. The saline solution contains 24% of potassium chloride and was adjusted to pH 5.0. The ionic strength of the aqueous solution is 3.21 moles/liter. 0.1% of lactose was further added for stabilization of the enzyme. After cooling, shaking is continued for another 2 hours at room temperature with addition of 0.5% of glutaraldehyde. This is followed by filtration by suction and washing. The lactase activities of support and filtrate are then compared. The support is found to have 34% of the initial activity, the filtrate, 11%.

Activity yield: 34%.

Use: The immobilized Aspergillus lactase is used as packing in a column reactor. At a temperature of 35° C., a lactose solution of pH 4.5 is hydrolyzed at a throughput rate of 40 fixed-bed volumes per hour with over 90% conversion. After 60 days, no loss of activity is observable.

EXAMPLE 3

Immobilized yeast lactase

Support: Macroporous, highly crosslinked bead polymer comprising methacrylamide/methylenebismethacrylamide having free epoxy groups (1.2% oxirane oxygen) and 2.2% of adhering isopropenyl groups which are concentrated on the inner surfaces of the pores. Pore volume, 3.4 ml/g. Average pore diameter, 20 nm. The preparation of this support is described in Example 2 of German patent publication 27 22 751.

Coupling of the adsorbed enzyme here is effected covalently by reaction with the epoxy groups simultaneously with adsorption of the enzyme under the influence of the high salt concentration.

Enzyme: Yeast lactase from *Saccharomyces (Kluyveromyces) lactis*, liquid preparation 5,000 neutral lactase units (NLU).

Coupling: 10 g of support are shaken at room temperature (23° C.) with 10 g of enzyme in 80 g of saline solution. The latter contains 16% of dibasic potassium phosphate, 7.9% of monobasic potassium phosphate and, for stabilization of the enzyme, 20 ppm of $MnCl_2 \cdot 4H_2O$. The solution has an ionic strength of 3.34 moles/liter. After 72 hours, filtration by suction and washing are carried out and the lactase activity of the filtrate is compared with that of the support. The support is found to have 55% of the initial activity and the filtrate 14%.

At 55%, the activity yield is very high in the case of this sensitive enzyme.

Use: The coupled yeast lactase is used as packing in a column reactor. At a temperature of 7° C., skim milk with 0.3% fat is passed through it for 20 days at a flow rate of 55 fixed-bed volumes per hour. The lactose contained in the milk is hydrolyzed to glucose and galactose, at first with 65% conversion, and after 20 days with 50% conversion.

EXAMPLE 4

Immobilized aminoacylase

Support: Macroporous highly crosslinked bead polymer comprising methacrylamide/methylenebismethacrylamide having free epoxy groups (1.2% oxirane oxygen) and 2.2% adhering isopropenyl groups which are concentrated on the inner surfaces of the pores. Pore volume, 3.4 ml/g. Average pore diameter, 20 nm. The preparing of this support is described in Example 2 of U.S. Pat. No. 4,208,309.

Enzyme: Powdered aminoacylase concentrate from an Aspergillus strain.

Activity: 23,000 U/g. Substrate: Acetyl-D, L-methionine.

Coupling: 10 g of support are shaken at 35° C. with 20 g of enzyme preparation in 80 ml of saline solution. The latter contains 14.2% of sodium sulfate and 24 ppm of $CoCl_2 \cdot 6H_2O$ and is adjusted to pH 7.0. Its ionic strength is 3 moles/liter, disregarding the salt content of the enzyme preparation.

After 8 hours, the support is filtered by suction and washed. The support is found to have 61% of the initial activity and the filtrate, 1%. The activity yield thus is 61%.

EXAMPLE 5

Binding of penicillinamidase to various supports 3.5 g portions of moist support material according to Table III are washed five times, each time with five times their volume of desalinated water, and then suction filtered on a porous glass plate. Then the support material is shaken at about 21° C. for 2 hours with 6.8 ml of an enzyme solution containing 676 international units (IU) of penicillinamidase from *E. coli* in 0.5 M of potassium phosphate buffer (pH 7.5, with 0.1% $NaN_3$). The ionic strength of the buffer solution is 1.5 moles/liter. After the addition of 0.136 ml of a 25% aqueous glutaraldehyde solution which had been stabilized with an ion exchange resin (Amberlite A 21), shaking is continued for 2 hours. The loaded support material is then placed on a porous glass filter and washed three times with 1 M NaOH and twice with 0.05 M sodium phosphate buffer (pH 7.5, with 0.1% $NaN_3$).

The enzymatic activity was determined by alkalimetric titration at pH 7.5 using penicillin G K (crude) as a substrate. For this purpose, 20 ml each of the 2% substrate solution in 0.05 M sodium phosphate solution at pH 7.5 were used and automatically titrated at 37° C. with 0.5 M sodium hydroxide solution. The results are presented in Table III.

TABLE III

| Support Material | | Activity of Immobilized penicillinamidase | |
|---|---|---|---|
| Chemical composition | Trade name | U/g moist weight | Activity Yield |
| (a) Crosslinked agarose | ("Sepharose-CL-4B") | 96 | 58 |
| (b) Octylated crosslinked agarose | ("Octyl-Sepharose-CL-4B") | 98 | 53 |
| (c) Phenylated crosslinked agarose | ("Phenyl-Sepharose CL-4B") | 168 | 91 |
| (d) Cross linked agarose substituted with diethylaminoethyl groups (cataionic) | ("DEAE-Sepharose-CL-6B") | 84 | 61 |
| (e) Carboxymethylated crosslinked agarose (anionic) | ("CM-Sepharose-CL-6B") | 94 | 48 |
| (f) Phenoxyacetylcellulose | | 77 | 59 |

TABLE III-continued

| Support Material | | Activity of Immobilized penicillinamidase | |
|---|---|---|---|
| Chemical composition | Trade name | U/g moist weight | Activity Yield |
| (g) Oxirane-polyacrylamide resin (according to U.S. 4,208,309, (Example 1), reacted with benzyl thiol | | 172 | 85 |
| (h) Polymethacrylimide ("Rohacell WF") foam, ground | | 70 | 45 |
| (i) Crosslinked polymethyl methacrylate/ glycol dimethacrylate copolymer**, weight ratio 90:10 | | 35 | 25 |
| (j) Crosslinked polymethyl methacrylate/ glycol dimethacrylate copolymer**, weight ratio 80:20 | | 55 | 37 |
| (k) Crosslinked polymethyl methacrylate/ glycol dimethacrylate copolymer**, weight ratio 60:40 | | 43 | 33 |
| (l) Crosslinked polystyrene with 10% divinylbenzene | | 57 | 42 |
| (m) Porous glass, ("Controlled Pore Glass 10") pore volume 0.75 cm³/g, average pore diameter 17 nm, inner surface area 107 m²/g | | 105 | 60 |

**Method of preparation: A solution of 1 part by weight of polyvinyl alcohol in 320 parts of water is heated to 50° C. in a stirred vessel and a mixture of 100 parts of monomers (methylmethacrylate and glycol dimethacrylate or styrene and divinylbenzene, respectively), 60 parts of n-heptane, and 1.4 parts of dibenzoyl peroxide is dispersed therein as droplets with stirring. During the 4-hour polymerization time, the temperature is held by cooling to a maximum of 75° C. After that, the solvent is distilled off over 1 hour at 36° C. The polymer beads formed are separated by filtration after cooling.

EXAMPLE 6

Binding of trypsin to "Phenyl-Sepharose"

3.5 g (moist weight) of "Phenyl-Sepharose" are pretreated as in Example 1. Then 150 mg of trypsin dissolved in 6.8 ml of 0.5M potassium phosphate buffer (pH 7.5, with 0.1% $NaN_3$) are added, followed by shaking at 23° C. for 2 hours. The ionic strength is 1.5 moles/liter. Immobilization of the adsorbed enzyme and further treatment are carried out as in Example 1.

The enzymatic activity was determined using casein and N-benzoyl-1-arginine ethyl ester hydrochloride (BAEE) as substrates.

| Results: | Using casein | 8.3 U/g moist weight |
|---|---|---|
| | Using BAEE | 311 U/g moist weight |

EXAMPLE 7

Production of support-bound lactase preparations 1 g portions of *Aspergillus oryzae* lactase "Lactase Preparation 2214 C Conc." having a strength of 30,000 U/g are dissolved in 40 ml portions of a 0.7 M $Na_2SO_4$ solution having an ionic strength of 2.1 moles/liter at pH 5.5. Portions of such solutions are then mixed in each case with 10 g of one of the carrier resins listed in Table IV and shaken for 20 hours at room temperature. 0.8 ml of 25% aqueous glutaraldehyde solution is then added and shaking is continued for 2 hours at room temperature. The preparations are separated by filtration and washed and the activity of the immobilized enzyme and of the enzyme found in the filtrate is determined and expressed in percent of the initial activity. The results are presented in Table IV.

TABLE IV

| Carrier Material | Activity | |
|---|---|---|
| | Immobilized lactase Activity yield (%) | Residual activity in filtrate (%) |
| (a) Weakly basic ion exchanger based on styrene/divinyl-benzene ("Amberlite IRA 93") | 17.5 | 0 |
| (b) Macroporous adsorber resin comprising poly-acrylate basis ("Amberlite XAD 7") | 29.5 | 18 |
| (c) Macroporous phenol-formaldehyde adsorber resin, weakly basic ("Duolite S 561") | 24.0 | 5 |
| (d) Macroporous phenol-formaldehyde adsorber resin, weakly basic ("Duolite S 587") | 26.0 | 4 |
| (e) Macroporous phenol-formaldehyde adsorber resin, nonionic ("Duolite S 761") | 22.0 | 6 |
| (f) Macroporous glass, pore volume | 42.4 | 8 |

TABLE IV-continued

| Carrier Material | Activity Immobilized lactase Activity yield (%) | Residual activity in filtrate (%) |
| --- | --- | --- |
| 0.75 cm$^3$/g, average pore diameter 17 nm, inner surface area 107 m$^2$/g ("Controlled Pore Glass CPG 10") | | |
| (g) Polymethacrylimide foam, ground ("Rohacell") | 31.0 | 0 |
| (h) Hydroxyl apatite (basic calcium phosphate), ground | 16.5 | 4 |

EXAMPLE 8

Production of support-bound lactase preparation:Crosslinker is added at the beginning of adsorption 1 g of lactase from Aspergillus oryzae ("Lactase Preparation 2214 C Conc.") having a strength of 30,000 U/g is dissolved in 40 ml of a 0.7 m Na$_2$SO$_4$ solution having a ionic strength of 2.1 moles/liter al pH 5.5. This solution is then mixed with 10 g of the carrier (b) out of Table IV. At the same time 0.8 ml of 25% aqueous glutaraldehyde solution is added and this suspension is shaken for 20 hours at room temperature.

Crosslinking happens here during adsorption.

The preparation ia separated by filtration and washed and the activity of the immobilized enzyme and of the enzyme found in the filtrate is determined as 25% respectively 4%.

EXAMPLE 9

Production of support-bound lactase preparation:Crosslinker is added before adsorption Example 8 is repeated, but the addition of the aqueous glutaraldehyde to the enzyme solution occurs 20 minutes before the carrier is added.

Crosslinking happens here before adsorption.

The activity of the immobilized enzyme and of the enzyme found in the filtrate is determined as 17%, respectively 0%.

What is claimed is:

1. A method for immobilizing a dissolved protein on a solid, macroporous, water insoluble support having pores of a diameter of at least 10 nanometers and a pore volume greater than 0.1 cm$^3$/g, in the presence of an electrolyte innocuous for said protein, which method comprises washing a supernatant aqueous solution of the protein over said support until the protein has been adsorbed onto the support, said solution having an ionic strength of the electrolyte of at least 0.15 mole/liter but insufficient to coagulate the protein from the solution, and adding to the electrolyte-containing solution, after adsorption of the protein onto the support, a water soluble coupling component effecting crosslinking of the protein adsorbed onto the support.

2. A method as in claim 1 wherein said support either has no covalently bound cationic groups or no more than 0.1 milliequivalent/gram of such groups.

3. A method as in claim 2 wherein said support has not more than 5 milliequivalent/gram of covalently bound anionic groups per gram of dry weight.

4. A method as in claim 3 wherein said support has not more than 0.1 milliequivalent of covalently bound ionic groups per gram of dry weight.

5. A method as in claim 1 wherein said support does not swell to more than twice its volume in an aqueous medium.

6. A method as in claim 5 wherein said support is in the form of beads.

7. A method as in claim 5 wherein said support is in the form of particles having a particle size of less than 10 mm.

* * * * *